United States Patent
Shimizu

[19]

[11] Patent Number: 6,136,024
[45] Date of Patent: Oct. 24, 2000

[54] ARTIFICIAL BLOOD VESSEL

[75] Inventor: Yasuhiko Shimizu, 39-676 Kohataogurayama, Uji-shi, Kyoto 611-0002, Japan

[73] Assignees: Yasuhiko Shimizu, Kyoto; Tapic International Co., Ltd., Tokyo, both of Japan

[21] Appl. No.: 09/319,527

[22] PCT Filed: Dec. 2, 1997

[86] PCT No.: PCT/JP97/04387

§ 371 Date: Jun. 4, 1999

§ 102(e) Date: Jun. 4, 1999

[87] PCT Pub. No.: WO98/24385

PCT Pub. Date: Jun. 11, 1998

[30] Foreign Application Priority Data

Dec. 6, 1996 [JP] Japan ................................. 8-326620

[51] Int. Cl.[7] ........................................................ A61F 2/06
[52] U.S. Cl. ................................................................ 623/1.47
[58] Field of Search .................................. 623/11, 15, 1, 623/1.42, 1.43, 1.44, 1.46, 1.47

[56] References Cited

U.S. PATENT DOCUMENTS 5,028,597 7/1991 Kadama et al. ............................ 623/11
5,723,010 3/1998 Yui et al. .................................... 623/15

FOREIGN PATENT DOCUMENTS

| 742020A2 | 11/1996 | European Pat. Off. |
| 4-146763 | 5/1992 | Japan . |
| 8-24326A | 1/1996 | Japan . |
| 8-294530 | 11/1996 | Japan . |

OTHER PUBLICATIONS

Copy of Int'l Search Report re PCT/JP97/04387 dated Feb. 24, 1998; and a copy of translation of same.

*Primary Examiner*—Michael Buiz
*Assistant Examiner*—Kevin Truong
*Attorney, Agent, or Firm*—David G. Conlin; Robert L. Buchanan; Dike, Bronstein, Roberts & Cushman, LLP

[57] ABSTRACT

The present invention provides an artificial blood vessel provided with collagen layer composed of ultra-fine fibers on at least the outside of a tube composed of a supporting framework material, and a method for producing the same. The present invention offers advantages such that its materials are easily acquired, it causes very little rejection after being transplanted into the body, it allows sutures to be maintained for a long time after transplant, and all or a portion is absorbed and degraded in the body after a predetermined period of time.

34 Claims, 1 Drawing Sheet

ARTIFICIAL BLOOD VESSEL

TECHNICAL FIELD

The present invention relates to an artificial blood vessel and a method for producing the same that can be used in the fields of human and veterinary medical care.

BACKGROUND ART

Artificial blood vessels are artificial organs used for the purpose of circulation repair in the field of vascular surgery. Since artificial blood vessels have the characteristic of being permanently implanted in the body, particularly rigid standards are required with respect to safety. In addition to not changing in size (e.g. dilation), not causing the occurrence of new aneurysms, ruptures and so forth, they are also required to have bioaffinity and be composed of materials having histocompatibility. As predecessors of the artificial blood vessels of today, artificial blood vessels for medical use have been developed over the past forty years and are currently available on the market. These include artificial blood vessels made of PET, those made of drawn polytetrafluoroethylene film (EPTFE) and those originating in living tissue. Other examples of products that have been developed include knit or woven artificial blood vessels made of PET (trade name: Dacron) or PTFE (Teflon), those in which artificial blood vessels are coated with collagen or gelatin (Hemashield or Zeroseal)in order to prevent bleeding from the mesh of these woven artificial blood vessels immediately after their replacement, and those that prevent bleeding and thrombus formation inside the vessel by coating the mesh of these woven artificial blood vessels with albumin. Artificial blood vessels made of EPTFE (trade name: Goatex) offer the advantage of making it difficult to form thrombi. On the other hand, with respect to those originating in living tissue, although there are some examples for which satisfactory patency is obtained by treating dog artery with surfactant (see Brandel, et al., Japanese Provisional Patent Publication No. 60-501540) to form a connective tissue tube followed by homotransplantation, these are still only at the experimental stage. In humans, although body tissue is used for transplantation by taking out congenic arteries and veins from cadavers followed by storing after freezing gradually to reduce isoimmunization, it is actually essential to use an immunosuppressant to avoid rejection. In addition, artificial blood vessels have also been developed in which human umbilical cord vein is crosslinked with a crosslinking agent, after which the outside thereof is coated with an extremely coarse Dacron mesh.

On the other hand, collagen is also known as a medical material, and this is used in combination with living tissue originating and artificial materials (see Japanese Provisional Patent Publication No. 2-109569 and Japanese Provisional Patent Publication No. 7-116242). Collagen has excellent bioaffinity, histocompatibility and low antigenicity, as well as action that promotes host cell extension and growth. It also has hemostatic action and is completely absorbed in the body. This collagen is obtained by extracting from various animals, and insoluble collagen is treated with base or enzyme. However, extracted collagen is in the form of monomers and oligomers at the molecular level, and is broken down extremely rapidly in water, humor and blood. Consequently, in order to use these collagens as medical materials, it is necessary that they be crosslinked with a crosslinking agent, gamma rays, ultraviolet rays, electron beam or heat to give them suitable physical properties prior to use. However, the use of powerful crosslinking agents results in a loss of the biochemical properties of the collagen. What is more, even if crosslinked in this manner, there is hardly any improvement in the tear strength of other physical properties of the collagen material. Consequently, in the case of using collagen in combination with other materials as an artificial organ, the needle holes in the sutured surface after being transplanted in the body end up enlarging as a result of being unable to withstand the load, ultimately resulting in rupture. As is indicated by this example, it has not been possible to produce products requiring specific physical properties. Artificial blood vessels composed by combining collagen with other materials also have the disadvantage of the sutured portion not being maintained for a long time in the body.

DISCLOSURE OF INVENTION

There is a need for an artificial blood vessel for use as a medical material for which its materials are easily acquired, causes very little rejection after being transplanted into the body, allows sutures to be maintained for a long time after transplant, and all or a portion is absorbed and degraded in the body after a predetermined period of time.

The applicant/inventor developed collagen having excellent physical properties, is able to withstand suturing, does not require the use of chemicals in the crosslinking procedure, and as a result, suffers no loss of its biochemical properties, and combined this collagen with a living tissue originating or artificial material easily obtainable and having low antigenicity, thereby leading to the acquisition of a novel artificial blood vessel of the present invention.

The present invention relates to an artificial blood vessel provided with collagen layer composed of ultra-fine fibers on at least the outside, and namely the outside or outside and inside, of a tube composed of a supporting framework material impregnated with a collagen solution, a collagen coated layer on its outside, and a matrix gel layer containing collagen on the tube lumen. The present invention also relates to a method for producing the same.

Various bulk materials can be used for the supporting framework material in the artificial blood vessel of the present invention. Examples of tubes composed of those materials include connective tissue tubes originating in the arteries or veins of humans or animals other than humans (e.g., dogs, pigs, cows), and particularly that originating in umbilical vein, connective tissue tubes originating in human subcutaneous tissue according to the Sparks-Mandrel method, tubes composed of non-degradable synthetic polymer mesh such as polyurethane, silicone or PET, and tubes composed of biodegradable and absorbable synthetic polymer mesh such as polyglycolic acid, polylactic acid, polydioxanone or copolymers of polyglycolic acid and polylactic acid and copolymers of polylactic acid and mol ε-caprolactone.

Tubes composed of arteries or veins of humans or animals other than humans used as the supporting framework material of the present invention are used in the present invention in the form of connective tissue tubes of biological origin after extracting these vessels, washing by ultrasonic treatment with sterile water containing protease inhibitor, treating with a tris buffercontaining non-ionic surfactant and protease inhibitor, manually removing adhered substances, additionally washing with sterile water, washing by ultrasonic treatment and thereby being purified. For example, in the case of human umbilical vein, only the vein having the larger diameter is used from human umbilical cord having a structure in which one artery and two veins are surrounded by Walton's colloid. Endothelial and adventitial cells are removed from this umbilical vein to reduce antigenicity and obtain a tube in the form of a connective tissue tube composed of collagenous fibers, elastic fibers and basement membrane. Namely, this tube has lower antigenicity and little risk of rejection during transplant. According to this method, umbilical cords discarded conventionally following childbirths can be used effectively, and since umbilical veins originate in fetuses, there is less risk of bacterial infection than the case of using blood vessels of adult humans (adult animals). In this way, in the case of using connective tissue tubes originating in blood vessels of humans or animals other than humans for artificial blood vessel materials, since tubes that inherently functioned as blood vessels are used as blood vessels after reducing antigenicity, they have excellent compliance required as blood vessels, are biocompatible and biodegradable, and in the case of using umbilical vein and so forth, it is possible to obtain narrow artificial blood vessels that were essentially unable to be achieved with conventional artificial materials due to the susceptibility of thrombus formation.

Here, the basement membrane in the connective tissue tube originating in an artery or vein of a human or animal other than a human has the role of promoting regeneration of recipient's endothelial cells by serving as the foundation for endothelial cell regeneration in the form of a cell guiding path following transplantation of the artificial blood vessel of the present invention into the body, and the connective tissue tube of the transplanted blood vessel is finally broken down, absorbed into the body, and replaced by cells of the recipient.

The tube composed of the connective tissue tube according to the Sparks-Mandrel method used in the present invention refers to a tube in which a rod-shaped object having the desired diameter of an artificial material such as silicone or PET is coated with a mesh made of silicone, PET or polyurethane, implanted for 4–8 weeks in subcutaneous tissue of a human (patient) followed by removal of that rod-shaped object along with a capsule-shaped connective tissue tube in which a collagenous fibers layer is formed around it. The membrane thickness of the tube can be controlled by adjusting the thickness of the mesh material as desired.

The tube composed of a synthetic polymer used in the present invention is a tube in which threads made of a polymer such as PET, polyurethane or silicone are woven into a mesh.

The tube composed of a biodegradable and absorbable synthetic polymer used in the present invention is a tube in which threads made of polyglycolic acid, polylactic acid, polydioxanone, copolymer of polyglycolic acid and polylactic acid or copolymer of polylactic acid and ε-caprolactone and so forth are woven into a mesh.

The artificial blood vessel of the present invention is that in which a tube composed of a supporting framework material composed of the above-mentioned bulk materials is treated by impregnating and coating with an extracted collagen solution. In the present invention, there are no particular restrictions on the origin of the collagen used to impregnate and coat the tube, and typically collagen can be used that is obtained from the skin, bone, cartilage, tendon or organs of mammals such as cows, pigs, rabbits, sheep, mice or birds.

The extracted collagen used in the present invention refers to that in which antigenicity has been reduced by extracting after protein decomposition of these tissues with acid, base or enzyme and so forth.

In order to impregnate collagen into the tube, the tube is immersed in a hydrochloric acid solution of extracted collagen (type I) followed by drying. Collagen molecules are dispersed throughout this hydrochloric acid solution of extracted collagen. As a result of performing this treatment, a structure is formed in the case of supporting framework material of biological origin in which collagen is incorporated between the connective tissue, thereby promoting cell growth following artificial blood vessel transplant.

As shown in FIGS. 1, 2 and 3, the artificial blood vessel of the present invention has compressed layer 2 composed of ultra-fine fibers of extracted collagen (type I) on the outsides of the above-mentioned extracted collagen-impregnated tubes 1, 5, or on the outside and inside of similar tube 6. Collagen molecules are not dispersed throughout this layer. Individual molecules gather to form ultra-fine fibers (diameter of about 5 nm), and these fibers then gather to form fine fibers (diameter of about 50 nm), and several of these gather to form narrow fibers (diameter of about 2 $\mu$m). Each of these narrow fibers then alternately overlap in the manner of warp and weft to form fibers having a diameter of about 6 $\mu$m, and a structure is formed in which these fibers are arranged in a fixed direction. Microscopically, this structure appears as a porous, non-woven fabric in the shape of compressed honeycombs. The thickness of the collagen layer having this structure is about 0.5–2.5 mm, and preferably about 1–2 mm. This collagen layer composed of ultra-fine fibers can be formed by freezing a layer composed of a hydrochloric acid solution of extracted collagen disposed around a connective tissue tube or synthetic polymer tube impregnated with extracted collagen and then dried followed by immediately by freeze-drying and then compressing it The artificial blood vessel of the present invention allows amorphous collagen to penetrate between the above-mentioned ultra-fine fibers by further impregnating a tube having collagen layer 2 composed of said ultra-fine fibers with extracted collagen (type I), and forming extracted collagen layer 3 on its outside, and thereby coating the collagen layer composed of ultra-fine fibers with a characteristic upright fiber surface. In this coating layer, collagen molecules do not form a fibrous structure, and instead exist in a dispersed, amorphous state.

After forming two collagen layers composed of an ultra-fine fiber layer on the outside or outside and inside of a collagen-impregnated tube, and an amorphous layer on top of it, in the manner described above, the artificial blood vessel of the present invention is obtained by thermal dehydration crosslinking the entire structure. This artificial blood vessel has a collagen layer having excellent physical properties that is obtained without using a crosslinking agent or other chemical substances and retains the biochemical properties of collagen. Since the collagen layer composed of ultra-fine fibers of the present invention obtained in this manner has strength that is able to withstand suturing that is not found in conventional collagen membranes, when transplanting the artificial blood vessel of the present invention, the sutures are well maintained even after being sutured to the recipient's blood vessel with surgical thread, and there is no problem associated with the prior art in which the portion of the collagen layer containing needle holes ruptures as a result of being unable to withstand the load.

Moreover, the lumen of the tube composed of a supporting framework material of the artificial blood vessel of the present invention is coated with matrix gel layer 4 containing collagen (type IV), which gives the function of promoting extension and regeneration of endothelial cells as a substitute for basement membrane, while also approaching blood vessels in the body. Tubes obtained by the Sparks-Mandrel method described above and tubes composed of two types of synthetic polymer mesh are used to form the artificial blood vessel of the present invention by forming the above-mentioned two collagen layers, and providing a matrix gel layer containing collagen, which is the basic component of the basement membrane, in both their lumen in place of a basement membrane layer. This matrix gel layer fulfills the same function as the basement membrane of human and animal blood vessels, and achieves the objective of promoting regeneration of recipient's endothelial cells in the case of transplanting artificial blood vessels. On the other hand, in the case of tubes composed of blood vessels of humans or animals other than humans as well, a matrix gel coating layer is also preferably provided on the surface of the basement membrane for the purpose of promoting rapid tissue extension and regeneration.

Figure 1:
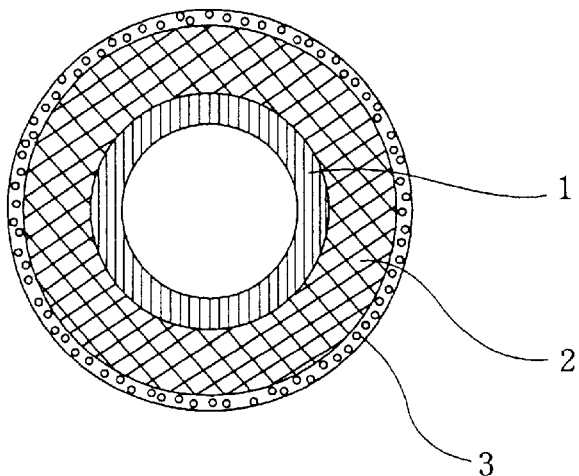
FIG. 1 is a cross-sectional schematic drawing (assuming a circular cross-section; to apply similarly hereinafter) of the artificial blood vessel of the present invention in the case of using a tube composed of animal artery or vein for the supporting framework material (furthermore, dimensions have been exaggerated to facilitate understanding of the structure of the present invention; to apply similarly hereinafter).
Figure 2:
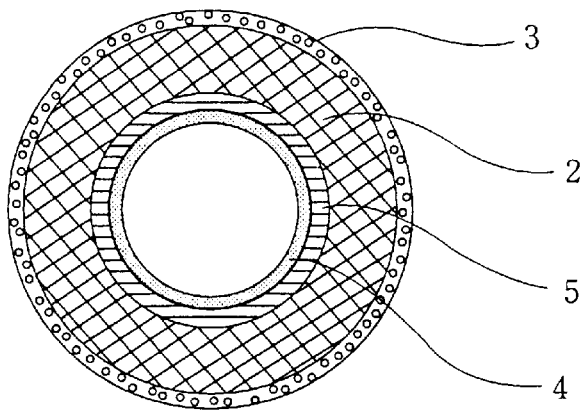
FIG. 2 is a cross-sectional schematic drawing of the artificial blood vessel of the present invention in the case of using a connective tissue tube originating in human (patient) subcutaneous tissue according to the Sparks-Mandrel method for the supporting framework material.
Figure 3:
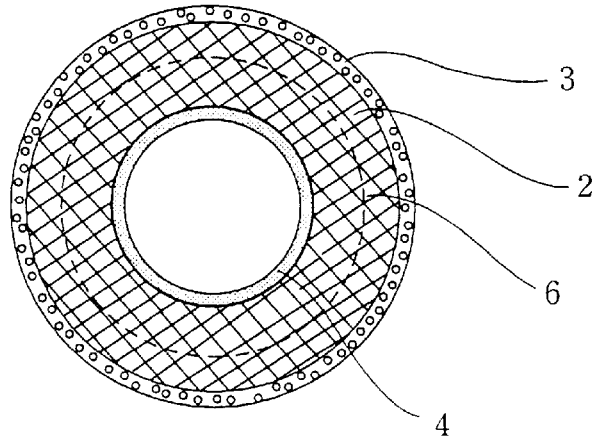
FIG. 3 is a cross-sectional schematic drawing of the artificial blood vessel of the present invention in the case of using a tube composed of non-degradable synthetic polymer mesh or biodegradable and absorbable synthetic polymer mesh for the supporting framework material.

In the drawings, the reference numerals represent the following:

1: Layer in which a layer of biological origin (basement membrane component+elastic fibers layer+collagenous fibers layer) is impregnated with extracted collagen;
2: Layer in which extracted collagen is formed into ultra-fine fibers;
3: Extracted collagen amorphous layer;
4: Matrix gel coating layer;
5: Layer in which a collagen fiber layer formed by subcutaneous implantation is impregnated with extracted collagen; and
6: Layer in which non-degradable synthetic polymer mesh or biodegradable and absorbable synthetic polymer mesh is impregnated with extracted collagen.

BEST MODE FOR CARRYING OUT THE INVENTION

The artificial blood vessel of the present invention is the one that a connective tissue tube originating in artery or vein of humans or animals other than humans (such as dogs, pigs or cows), and particularly originating in umbilical vein, a connective tissue tube originating in human subcutaneous tissue according to the Sparks-Mandrel method, a tube composed of non-degradable synthetic polymer mesh such as polyurethane, silicone or PET, or a tube composed of biodegradable and absorbable synthetic polymer mesh such as polyglycolic acid, polylactic acid, polydioxanone, copolymers of polyglycolic acid and polylactic acid and copolymers of polylactic acid and $\epsilon$-caprolactone, are coated with a plurality of collagen layers thereon.

A 1 N hydrochloric acid solution (pH=3) containing about 0.5–3 wt % of extracted collagen is impregnated into a tube composed of this type of supporting framework material to allow the collagen to penetrate into the supporting framework material followed by drying. Impregnation time is 12–48 hours and preferably 24 hours. The concentration of extracted collagen is most preferably 0.5 wt %. As a result of this treatment, regeneration of cells is promoted following transplantation of the artificial blood vessel due to collagen molecules being incorporated in the supporting framework. This step is repeated 1–5 times.

A glass or silicone rod is passed through the tube composed of the supporting framework material following collagen impregnation and drying, the tube inserted the rod therein is placed upright in a container containing 1 N hydrochloric acid solution (pH=3) containing about 0.5–3 wt %, and particularly 1 wt %, of extracted collagen, after which it is frozen in that state for about 6–48 hours, preferably at least 12 hours, and particularly preferably 24 hours, at preferably −10 to −196° C., and particularly preferably about −20° C. At this time, collagen composed of ultra-fine fibers is formed in the frozen collagen layer on the outside or outside and inside of the tube.

The tube composed of the above-mentioned supporting framework material on which the frozen collagen solution layer is formed on its outside or outside and inside is immediately freeze-dried without returning to normal temperature to vaporize the water. The collagen layer demonstrates a layered structure composed of ultra-fine fibers and is in the form of a non-woven fabric. The thickness of the ultra-fine fibrous collagen layer formed at this time is adjusted to be about 0.5–2.5 cm, and preferably about 1–2 cm.

The tube of the above-mentioned supporting framework material provided with a layer composed of ultra-fine fibrous collagen obtained in the manner described above is compressed with a pressing apparatus with the glass or silicone rod still passing through it. The compression conditions at this time are such that the compression ratio, namely the ratio of the thickness of the collagen layer after pressing to the thickness of the collagen layer before pressing, is 0.005–0.3, and preferably 0.1. The collagen layer composed of ultra-fine fibers obtained in this manner has physical properties not found in conventional collagen membranes.

A procedure consisting of immersing the collagen-coated tube obtained in the above manner in a 1 N hydrochloric acid solution containing about 0.5–3 wt %, and particularly 2 wt %, of extracted collagen followed by drying is repeated 1–20 times corresponding to the strength of the vessel wall desired, amorphous collagen is impregnated between the ultra-fine fibers, and an amorphous collagen layer is also cast on the ultra-fine fiber layer.

The tube obtained in this manner is then subjected to crosslinking treatment. Although crosslinking methods including gamma ray crosslinking, electron beam crosslinking, ultraviolet ray crosslinking, thermal dehydration crosslinking, glutaraldehyde crosslinking, epoxy crosslinking and water-soluble carbodiimide crosslinking can be used, thermal dehydration crosslinking is preferable since control of the degree of crosslinking is easy while effects on the body is minimized as a result of not using chemical substances for crosslinking treatment. Thermal dehydration crosslinking treatment is performed in a vacuum at about 105–150° C., and preferably 120–150° C., for about 6–48 hours, and preferably 6–24 hours. For example, the greatest crosslinking density is obtained in the case of treating at 140° C. for 48 hours, and the degrees of crosslinking is 85–90%. The glass or silicone rod is removed after crosslinking treatment to obtain an artificial blood vessel composed of a supporting framework material coated with collagen. The retention time of the artificial blood vessel of the present invention in the body after transplant can be adjusted by adjusting the temperature and duration of crosslinking treatment at this time.

Furthermore, this thermal dehydration crosslinking may be performed twice, namely once before or after the above-mentioned compression step, and once more after casting of the amorphous collagen.

Moreover, the artificial blood vessel of the present invention can be given a function similar to the basement membrane of a blood vessel in the body by coating the lumen of the tube with a matrix gel immediately after performing thermal crosslinking treatment. This matrix gel contains collagen (particularly type IV, for example, 30 wt %), laminin (for example, 50–60 wt %), heparan sulfate proteoglycans (for example, 2–5 wt %), entactin (for example, 5–10 wt %) as well as EGF (epithelium growth factor), βFGF (fibroblast growth factor), NGF (nerve growth factor), PDGF (platelet-derived growth factor), IGF-1 (insulin-like growth factor), TGF-β (transforming growth factor) and so forth that serves as the foundation for extension and regeneration by recipient's endothelial cells, and the lumen of the tube is coated by method consisting of dipping the tube in a 10 wt % aqueous solution of this gel for 60 minutes at room temperature and drying it.

The collagen layer formed on the outside or outside and inside of a tube composed of a supporting framework material in this manner is present in the body for a fixed period of time after the artificial blood vessel of the present invention is transplanted into the body, and during that time, is replaced by growth of recipient's tissue. In the case of a tube originating in umbilical vein, ultimately endothelial cells regenerate and grow by using the basement membrane portion of the lumen surface as a foundation until all endothelial cells are rebuilt and regenerated as the recipient's own blood vessel tissue. In general, a tube originating in humans or animals other than humans are degraded and absorbed by the body 6–10 weeks after transplant, and in the case of biodegradable and absorbable synthetic polymer mesh, are degraded and absorbed 6–8 weeks after transplant.

Although the following provides an example of the present invention, this example does not limit the present invention.

EXAMPLE 1

Artificial Blood Vessel Using Human Umbilical Vein

Umbilical vein was excised from human umbilical cord followed by washing for 48 hours at room temperature or 40° C. with a 1% aqueous solution of Triton X-100, and additionally washing for 48 hours under running water. Thus obtained connective tissue tube originating in umbilical vein was immersed in a 1 wt % aqueous collagen solution and dried, and this procedure was repeated five times. This tube was then allowed to stand upright in a 1 N hydrochloric acid solution containing 1 wt % collagen with a support rod passing through it, followed by freezing for 24 hours at −20° C. Next, the frozen tube was then freeze-dried to form an ultra-fine fibrous layer having a thickness of 10 mm. This was then compressed at 50 kg to form a tube having a thickness of 1 mm. This was then immersed in a 1 wt % aqueous collagen solution and then dried, and this procedure was repeated 10 times. Next, thus obtained tube was thermal dehydration crosslinked for 12 hours at 140° C. to obtain the artificial blood vessel of the present invention. Three centimeters in dog carotid artery were replaced with this artificial blood vessel. The animal was then sacrificed two and a half months after transplant and the transplantation site was observed microscopically. As a result, the artificial blood vessel was confirmed to have been replaced by the dog's own blood vessel tissue.

Industrial Applicability

The artificial blood vessel of the present invention offers advantages including (1) the absence of the occurrence of rejection since it uses a portion of a material originating in body tissue having low antigenicity or uses an artificial material having low antigenicity, (2) the ability to withstand pressure and allow suturing using surgical thread that was not possible in the case of conventional collagen membranes since a collagen layer is present that is formed to be composed of ultra-fine fibers, and (3) allows regeneration of recipient's endothelial cells on the surface of the lumen since a biological basement membrane portion or an alternative material is present on the surface of that lumen.

What is claimed is:

1. An artificial blood vessel comprising a collagen layer composed of ultra-fine fibers made of an extracted collagen and formed on at least the outside of a tube composed of a supporting framework material.

2. The artificial blood vessel according to claim 1, wherein an extracted collagen amorphous layer is additionally formed on the outside of the collagen layer composed of ultra-fine fibers made of an extracted collagen and formed on at least the outside of the tube.

3. The artificial blood vessel according to claim 2, wherein the tube is a tube impregnated with an extracted collagen.

4. The artificial blood vessel according to claim 2, wherein the lumen of the tube is coated with a matrix gel.

5. The artificial blood vessel according to claim 2, wherein said collagen layer composed of ultra-fine fibers has a structure in which several collagen molecules gather to form ultra-fine fibers having a diameter of about 5 nm, the fibers further gathering to form fine fibers having a diameter of about 50 nm, several of the fibers further gathering to form narrow fibers having a diameter of about 2 μm, each of these narrow fibers then overlapping in a manner of warp and weft to form fibers having a diameter of about 6 μm; wherein the fibers are arranged in a fixed direction.

6. The artificial blood vessel according to claim 5, wherein the tube is a tube impregnated with an extracted collagen.

7. The artificial blood vessel according to claim 5, wherein the lumen of the tube is coated with a matrix gel.

8. The artificial blood vessel according to claim 2, wherein the supporting framework material is a connective tissue tube of biological origin composed of collagenous fibers, elastic fibers and basement membrane.

9. The artificial blood vessel according to claim 8, wherein the collagen layer composed of ultra-fine fibers has a structure in which several collagen molecules gather to form ultra-fine fibers having a diameter of about 5 nm, the fibers further gathering to form fine fibers having a diameter of about 50 nm, several of the fibers further gathering to form narrow fibers having a diameter of about 2 µm, each of these narrow fibers then overlapping in a manner of warp and weft to form fibers having a diameter of about 6 µm; wherein the fibers are arranged in a fixed direction.

10. The artificial blood vessel according to claim 2, wherein the supporting framework material is a connective tissue tube originating in human subcutaneous tissue according to the Sparks-Mandrel method.

11. The artificial blood vessel according to claim 10, wherein the collagen layer composed of ultra-fine fibers has a structure in which several collagen molecules gather to form ultra-fine fibers having a diameter of about 5 nm, the fibers further gathering to form fine fibers having a diameter of about 50 nm, several of the fibers further gathering to form narrow fibers having a diameter of about 2 µm, each of these narrow fibers then overlapping in a manner of warp and weft to form fibers having a diameter of about 6 µm; wherein the fibers are arranged in a fixed direction.

12. The artificial blood vessel according to claim 1, wherein the tube is a tube impregnated with an extracted collagen.

13. The artificial blood vessel according to claim 12, wherein the lumen of the tube is coated with a matrix gel.

14. The artificial blood vessel according to claim 1, wherein the lumen of the tube is coated with a matrix gel.

15. The artificial blood vessel according to claim 1, wherein the collagen layer composed of ultra-fine fibers has a structure in which several collagen molecules gather to form ultra-fine fibers having a diameter of about 5 nm, the fibers further gathering to form fine fibers having a diameter of about 50 nm, several of the fibers further gathering to form narrow fibers having a diameter of about 2 µm, each of these narrow fibers then overlapping in a manner of warp and weft to form fibers having a diameter of about 6 µm; wherein the fibers are arranged in a fixed direction.

16. The artificial blood vessel according to claim 15, wherein the tube is a tube impregnated with an extracted collagen.

17. The artificial blood vessel according to claim 15, wherein the lumen of the tube is coated with a matrix gel.

18. The artificial blood vessel according to claim 1, wherein the supporting framework material is a connective tissue tube of biological origin composed of collagenous fibers, elastic fibers and basement membrane.

19. The artificial blood vessel according to claim 18, wherein the collagen layer composed of ultra-fine fibers has a structure in which several collagen molecules gather to form ultra-fine fibers having a diameter of about 5 nm, the fibers further gathering to form fine fibers having a diameter of about 50 nm, several of the fibers further gathering to form narrow fibers having a diameter of about 2 µm, each of these narrow fibers then overlapping in a manner of warp and weft to form fibers having a diameter of about 6 µm; wherein the fibers are arranged in a fixed direction.

20. The artificial blood vessel according to claim 1, wherein the supporting framework material is a connective tissue tube originating in human subcutaneous tissue according to the Sparks-Mandrel method.

21. The artificial blood vessel according to claim 10, wherein the collagen layer composed of ultra-fine fibers has a structure in which several collagen molecules gather to form ultra-fine fibers having a diameter of about 5 nm, the fibers further gathering to form fine fibers having a diameter of about 50 nm, several of the fibers further gathering to form narrow fibers having a diameter of about 2 µm, each of these narrow fibers then overlapping in a manner of warp and weft to form fibers having a diameter of about 6 µm; wherein the fibers are arranged in a fixed direction.

22. The artificial blood vessel according to claim 1, wherein the supporting framework material is a tube composed of a mesh material selected from the group consisting of polyurethane, silicone, PET, polyglycolic acid, polylactic acid, polydioxanone, polyglycolic acid-polylactic acid copolymer or polylactic acid-ε-caprolactone copolymer.

23. The artificial blood vessel according to claim 22, wherein the tube is a tube impregnated with an extracted collagen.

24. The artificial blood vessel according to claim 22, wherein the lumen of the tube is coated with a matrix gel.

25. The artificial blood vessel according to claim 22, wherein the collagen layer composed of ultra-fine fibers has a structure in which several collagen molecules gather to form ultra-fine fibers having a diameter of about 5 nm, the fibers further gathering to form fine fibers having a diameter of about 50 nm, several of the fibers further gathering to form narrow fibers having a diameter of about 2 µm, each of these narrow fibers then overlapping in a manner of warp and weft to form fibers having a diameter of about 6 µm; wherein the fibers are arranged in a fixed direction.

26. The artificial blood vessel according to claim 2, wherein the supporting framework material is a tube composed of a mesh material selected from the group consisting of polyurethane, silicone, PET, polyglycolic acid, polylactic acid, polydioxanone, polyglycolic acid-polylactic acid copolymer or polylactic acid-ε-caprolactone copolymer.

27. The artificial blood vessel according to claim 26, wherein the tube is a tube impregnated with an extracted collagen.

28. The artificial blood vessel according to claim 26, wherein the lumen of the tube is coated with a matrix gel.

29. The artificial blood vessel according to claim 26, wherein the collagen layer composed of ultra-fine fibers has a structure in which several collagen molecules gather to form ultra-fine fibers having a diameter of about 5 nm, the fibers further gathering to form fine fibers having a diameter of about 50 nm, several of the fibers further gathering to form narrow fibers having a diameter of about 2 µm, each of these narrow fibers then overlapping in a manner of warp and weft to form fibers having a diameter of about 6 µm; wherein the fibers are arranged in a fixed direction.

30. An artificial blood vessel comprising a collagen layer composed of ultra-fine fibers formed on at least the outside of a tube composed of a supporting framework material; wherein the ultra-fine fibers are produced by a method comprising freezing and freeze-drying the collagen layer.

31. The artificial blood vessel of claim 30, wherein the thickness of fibers formed during the freeze-drying is about 0.5 to 2.5 cm.

32. The artificial blood vessel of claim 31, wherein the method of producing the ultra-fine fibers further comprises the step of compressing the fibers.

33. The artificial blood vessel of claim 32, wherein the ratio of thickness of the collagen layer after the compression step to the thickness of the collagen layer before the compression step is about 0.005 to 0.3.

34. The artificial blood vessel of claim 30, wherein the ultra-fine fibers have diameter of between about 5 nm to 6µ.

* * * * *